United States Patent
Riehle et al.

(10) Patent No.: US 7,227,147 B2
(45) Date of Patent: Jun. 5, 2007

(54) PROCESS FOR MONITORING AND CONTROLLING NITRATING PROCESSES WITH THE AID OF AN ONLINE SPECTROMETER

(75) Inventors: Claus Riehle, Odenthal (DE); Marcus Brand, Dormagen (DE); Frank Hilgers, Dormagen (DE); Klaus Jäger, Leverkusen (DE); Rainer Giesen, Krefeld (DE); Heinz-Josef Hamacher, Bedburg (DE); Udo Wolf, Kempen (DE)

(73) Assignee: Bayer MaterialScience AG, Leverkusen (DE)

( * ) Notice: Subject to any disclaimer, the term of this patent is extended or adjusted under 35 U.S.C. 154(b) by 231 days.

(21) Appl. No.: 10/769,997

(22) Filed: Feb. 2, 2004

(65) Prior Publication Data
US 2004/0164247 A1   Aug. 26, 2004

(30) Foreign Application Priority Data
Feb. 5, 2003   (DE) ................................ 103 04 615

(51) Int. Cl.
*G01J 5/02* (2006.01)
(52) U.S. Cl. ............................................ 250/339.12
(58) Field of Classification Search ............ 250/339.12
See application file for complete search history.

(56) References Cited
U.S. PATENT DOCUMENTS

| | | | |
|---|---|---|---|
| 5,121,337 A | 6/1992 | Brown | 364/498 |
| 5,679,873 A | 10/1997 | Klingler et al. | 568/934 |
| 6,072,576 A | 6/2000 | McDonald et al. | 356/300 |
| 6,103,934 A * | 8/2000 | Hallinan et al. | 562/517 |
| 6,561,010 B2 * | 5/2003 | Wilson et al. | 73/54.04 |
| 6,810,718 B2 * | 11/2004 | Wilson et al. | 73/54.01 |
| 2004/0249512 A1 * | 12/2004 | Meeuwssen et al. | 700/270 |

OTHER PUBLICATIONS

David Firth, Nitration Reactions in the manufacture of Pharamceutircal Intermediates, Jan. 2001, Innovations in Pharamceutical Technology, pp. 132-139.*

* cited by examiner

*Primary Examiner*—Constantine Hannaher
*Assistant Examiner*—Christine Sung
(74) *Attorney, Agent, or Firm*—Joseph C. Gil; Lyndanne M. Whalen

(57) ABSTRACT

A process for monitoring and/or controlling a nitrating process, having the following steps:
  measuring inline infrared spectra of nitric acid content in a reaction mixture stream downstream of the nitration reaction, preferably near-infrared spectra,
  evaluating the measured spectra by means of a computer-assisted, matrix-specific calibration model for the purpose of determining the content of nitric acid,
  transmitting the results of spectrometric examination to a process control system,
  inputting the results of spectrometric examination for the purpose of specifying the content of nitric acid in the acid phase into a regulator (224) for control of the metering (207,217) of nitric acid into a nitrating reactor.

24 Claims, 5 Drawing Sheets

PROCESS FOR MONITORING AND CONTROLLING NITRATING PROCESSES WITH THE AID OF AN ONLINE SPECTROMETER

BACKGROUND OF THE INVENTION

The present invention relates to a process for monitoring and for controlling a nitrating process, in particular for the nitration of toluene, with the aid of a computer-assisted, matrix-specific calibration model and a process model.

Various nitration processes are known in the prior art. For example, toluene is nitrated with nitric acid to yield nitrotoluidines by way of intermediate dye products. It is also known to nitrate toluene with mixed acids to yield nitrotoluene and dinitrotoluene. Dinitrotoluene is, for example, processed further to yield diamines, diisocyanates, trinitrotoluene or phloroglucinol.

For economic reasons, the aim in the course of nitration is to conduct the nitration with as small an excess of acid as possible. To this end, it is known from the state of the art to take samples from the process manually and to examine them analytically in the laboratory. The process is then readjusted manually when required.

One disadvantage of such manual sampling and adjustment is the high cost of labor for the sampling and for the laboratory analysis. Another disadvantage is that the effort increases linearly with the number of measuring-points. Furthermore, manual sampling is problematic from the point of view of industrial safety, since, particularly in the case of 2-nitrotoluene, it is a question of working with a substance that is detrimental to health. Therefore in the course of handling 2-nitrotoluene, the wearing of respiratory protection at all times as a precaution is prescribed.

Another disadvantage of manual sampling with subsequent laboratory analysis is the fact that readjustment of the process can only be effected irregularly and after relatively long time-intervals. This may result in use of a relatively large excess of acid; the plant cannot then be operated in optimal manner, either technically or economically.

SUMMARY OF THE INVENTION

An object of the present invention is therefore to create an improved process for monitoring and controlling nitrating processes that enables a diminution of the excess of acid. Further objects underlying the invention are to create an online method of measurement with a computer-assisted process model and to create an appropriate production process for the nitration.

The objects of the present invention are achieved by online spectrometric measurement of the acid phase from the reaction mixture and transmission of that data to a process control system.

DETAILED DESCRIPTION OF THE INVENTION

Figure 1:
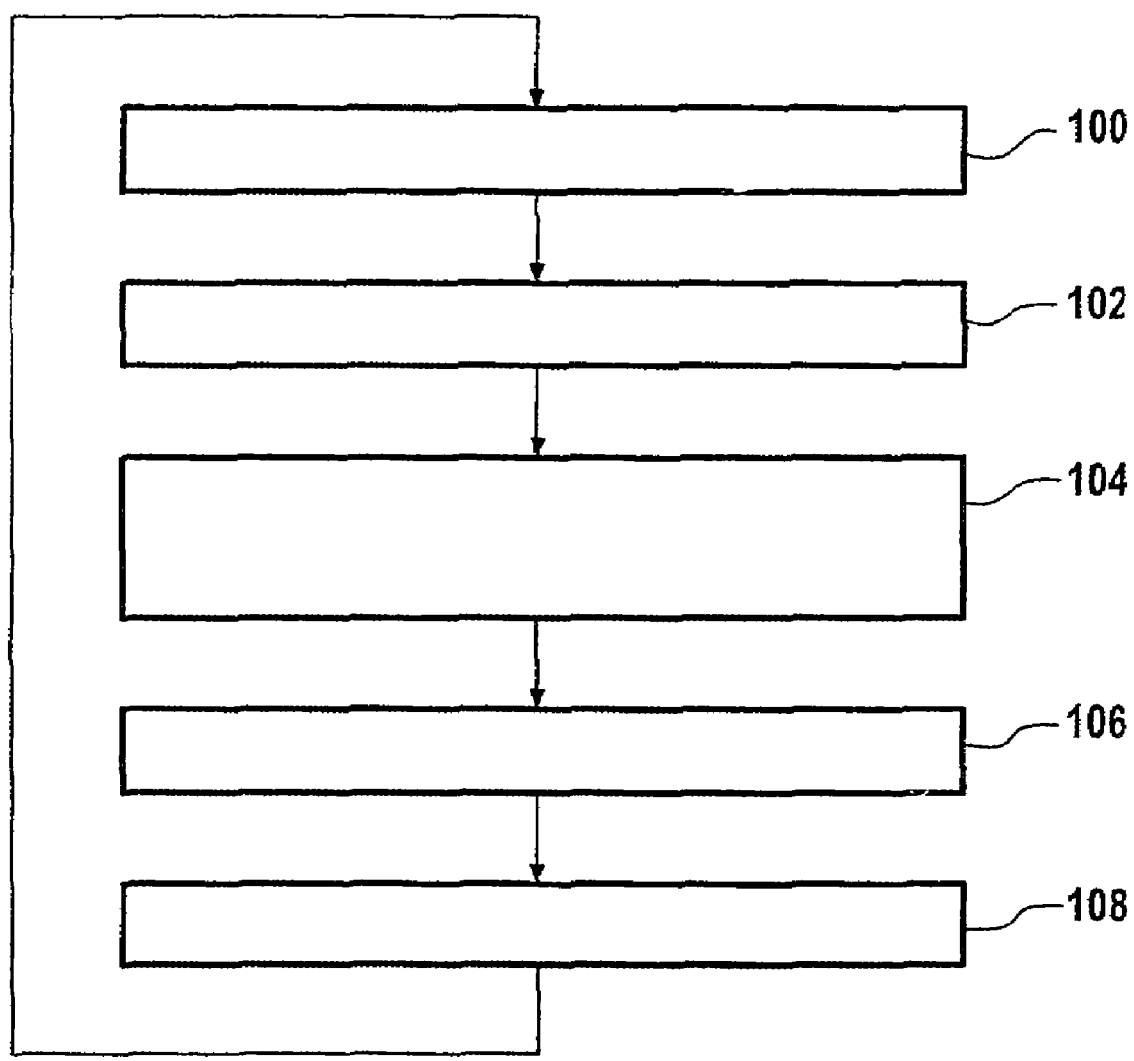
FIG. 1 is a flow chart for the process of the present invention for improved monitoring and control of nitrating processes by virtue of the online measurement of the acid phase and the improved metering of nitric acid.

In accordance with the present invention, the acid phase recovered from the nitration reaction mixture is spectrometrically examined online. This is preferably done by infrared spectrometry. Such measurements are also designated as infrared spectroscopy. Appropriate IR spectrometers, in particular for the near-infrared range (NIR) are commercially available, for example from Polytec GmbH and other manufacturers.

In a preferred embodiment of the invention, the content of nitric acid in the acid phase is determined online after nitration by means of an NIR spectrometer and a suitable computer-assisted calibration model. Data for quantifying the content of nitric acid are then transmitted from the NIR spectrometer to the process control system, for example via a field bus. On the basis of the nitric-acid content in the acid phase that is determined after nitration, regulation by the process control system for the supply of nitric acid is possible. The online control of a production plant for the purpose of regulating various polymerization parameters is disclosed in U.S. Pat. No. 5,121,337 and EP-0 948 761 B1 [sic]. In these disclosed processes, a predictive model created on the basis of measured spectra is used.

In a particularly preferred embodiment of the invention, the measured NIR spectrum is evaluated with the aid of a matrix-specific calibration model. The physical matrix is predetermined by the nitrating process and is dependent on the parameters of the process. With the aid of chemometric methods, the measured spectra are referenced against results obtained from laboratory examinations.

This is effected in such a way that the same sample for which an NIR spectrum was determined online is also analyzed in the laboratory with the aid of titration measurements. By virtue of the examination and the comparison of a suitable number of varying samples, it is possible to create a matrix-specific calibration model with the aid of chemometry. This matrix-specific calibration model is stored on a computer that is programmed to control the recording of the spectrum and to evaluate the measured spectrum online with the aid of the calibration model, so that the nitric acid content is available to the process control system online.

The nitration of toluene to yield dinitrotoluene (DNT) is generally conducted in two stages. The spectrometric examination of the acid phase is undertaken at least after the second nitrating stage, in order to readjust the supply of nitric acid to the first and/or the second nitrating stage.

In another preferred embodiment of the invention, the NIR spectrometer is connected to several measuring-points. The NIR spectrometer is multiplexed, in order to carry out spectrometric measurements in succession at the various measuring-points. By reason of this multiplex operation of the NIR spectrometer, the measurement effort increases degressively with the number of measuring-points.

The invention is particularly advantageous because it enables distinctly improved process control. In particular, the invention enables the production plant to be operated continuously, close to the technical and economic optimum. Another advantage is the improvement in industrial safety.

Preferred embodiments of the invention will be elucidated in greater detail below with reference to the drawings.

FIG. 1 is a flow chart for a process according to the invention for monitoring and controlling nitrating processes. In step 100, nitric acid ($HNO_3$) is supplied continuously to a nitrating stage. The product of the nitrating stage is a two-phase system composed of nitrated organic phase and acid phase. An NIR spectrum of the acid phase is recorded by means of a suitable measuring cell and an NIR spectrometer. This is undertaken in step 102. In step 104, the $HNO_3$ content in the acid phase is determined by evaluation of the NIR spectrum by means of a matrix-specific calibration model. This measurement is preferably undertaken inline or online, i.e. in the current product stream.

In step 106, the $HNO_3$ content that has been ascertained is transmitted to a process control system. In step 108, the quantity of continuously supplied $HNO_3$ is readjusted manually or by the process control system, in order to reduce the $HNO_3$ content in the acid phase if necessary.

Figure 2:
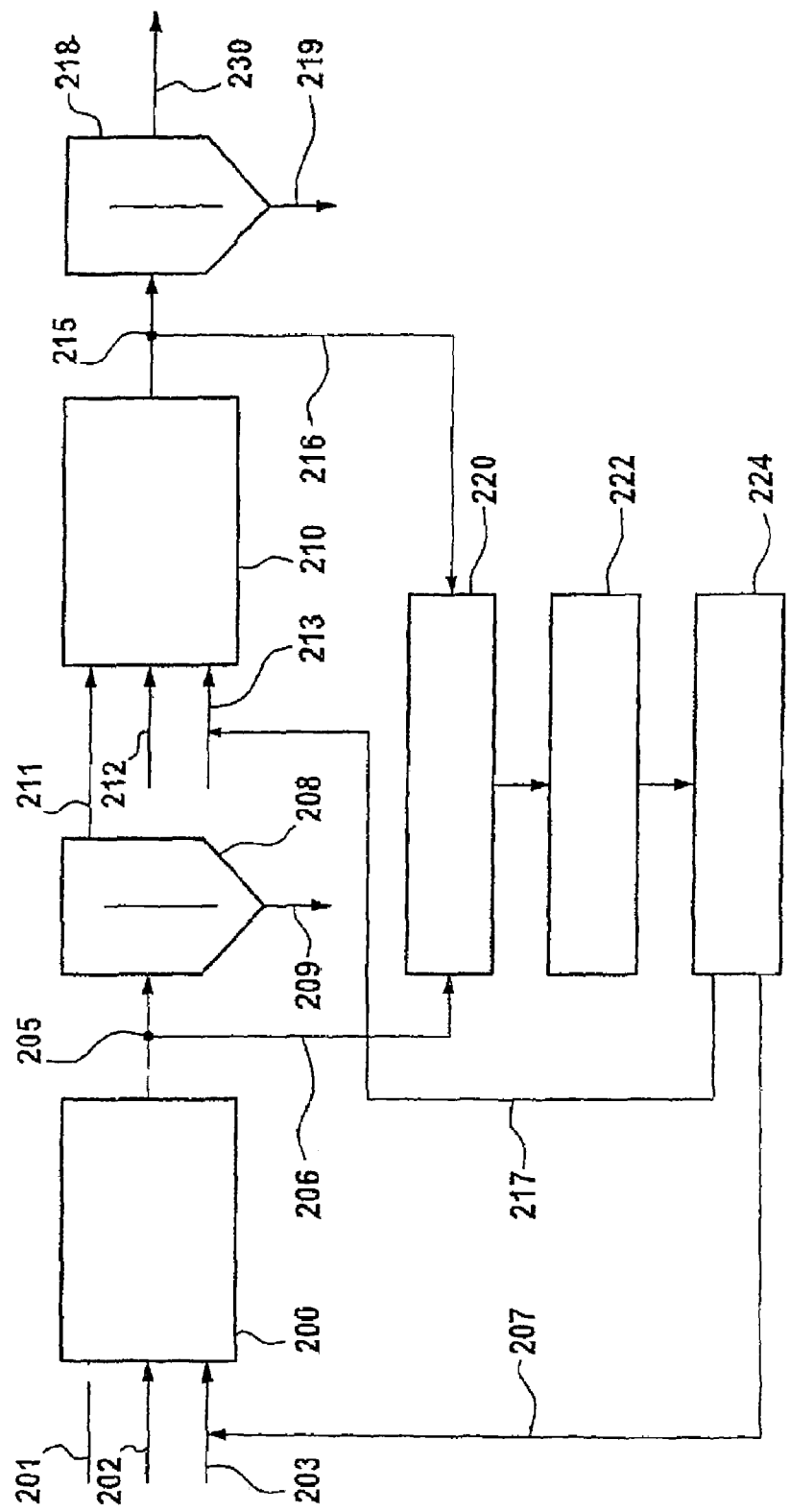
FIG. 2 is a block diagram of a two-stage nitration process according to the invention.

FIG. 2 is a block diagram of an embodiment of an appropriate plant. The plant has a reactor 200 for the purpose of realizing a first nitrating stage (mononitration MNT). The feed materials are toluene 201, sulfuric acid 202 and nitric acid 203. The product of the first nitrating stage is a two-phase system which is separated, in the separator 208 connected downstream, into the organic phase 211 and the acid phase 209.

A measuring-point 205 for recording an NIR spectrum of the acid phase may be provided downstream of the reactor 200. To this end, an NIR spectrometer 220 may be connected to the measuring-point 205 via an optical waveguide 206.

The separator 208 is followed by a further reactor 210 for the purpose of realizing the second nitrating stage (dinitration DNT). The feed materials are MNT 211, sulfuric acid 212 and nitric acid 213. The product of the second nitrating stage is a two-phase system which is separated, in the separator 218 connected downstream, into the organic phase 230 and the acid phase 219.

A measuring-point 215 is preferably arranged downstream of the output of the reactor 210. The NIR spectrometer 220 is connected to the measuring-point 215 via an optical waveguide 216. As a result, NIR spectra for the acid phase can be recorded.

The measuring-points 205 and 215 may each be operated with their own spectrometer; however, they are preferably operated with a single spectrometer 220 which switches between the measuring-points 205 and 215.

The NIR spectrometer 220 passes on the measured NR spectra for evaluation by means of the matrix-specific computer-assisted calibration model 222. The computer with the matrix-specific calibration model 222 passes on its results for the content of nitric acid to the process control system 224. The subsequent regulation (manual or automated) of the metering 207 or 217 of the first 200 and/or the second 210 nitrating stage, respectively, permits improved monitoring of the process and improved process control for the content of $HNO_3$ in the acid phase within the range 0–5%, in particular close to 0%, preferably within the range from 0% to 0.3%.

In a preferred embodiment of the invention, the $HNO_3$ content is determined only at measuring-point 215 and not at measuring-point 205. The measurement of the $HNO_3$ content at measuring-point 215 after the second nitrating stage is generally sufficient for regulation of the production of dinitrotoluene.

In the case where production of dinitrotoluene is undertaken in multiple lines, several parallel measuring-points 215 may be provided. All the measuring-points 215 are then preferably connected to the same NIR spectrometer 220, which operates in multiplex mode. The NIR spectrometer 220 accordingly measures the spectra at the measuring-points 215 in succession, in cyclic sequence. By virtue of the multiplexing of the NIR spectrometer 220, it is possible for the instrumentation effort for implementation of the $HNO_3$ measurements to be optimized.

Figure 3:
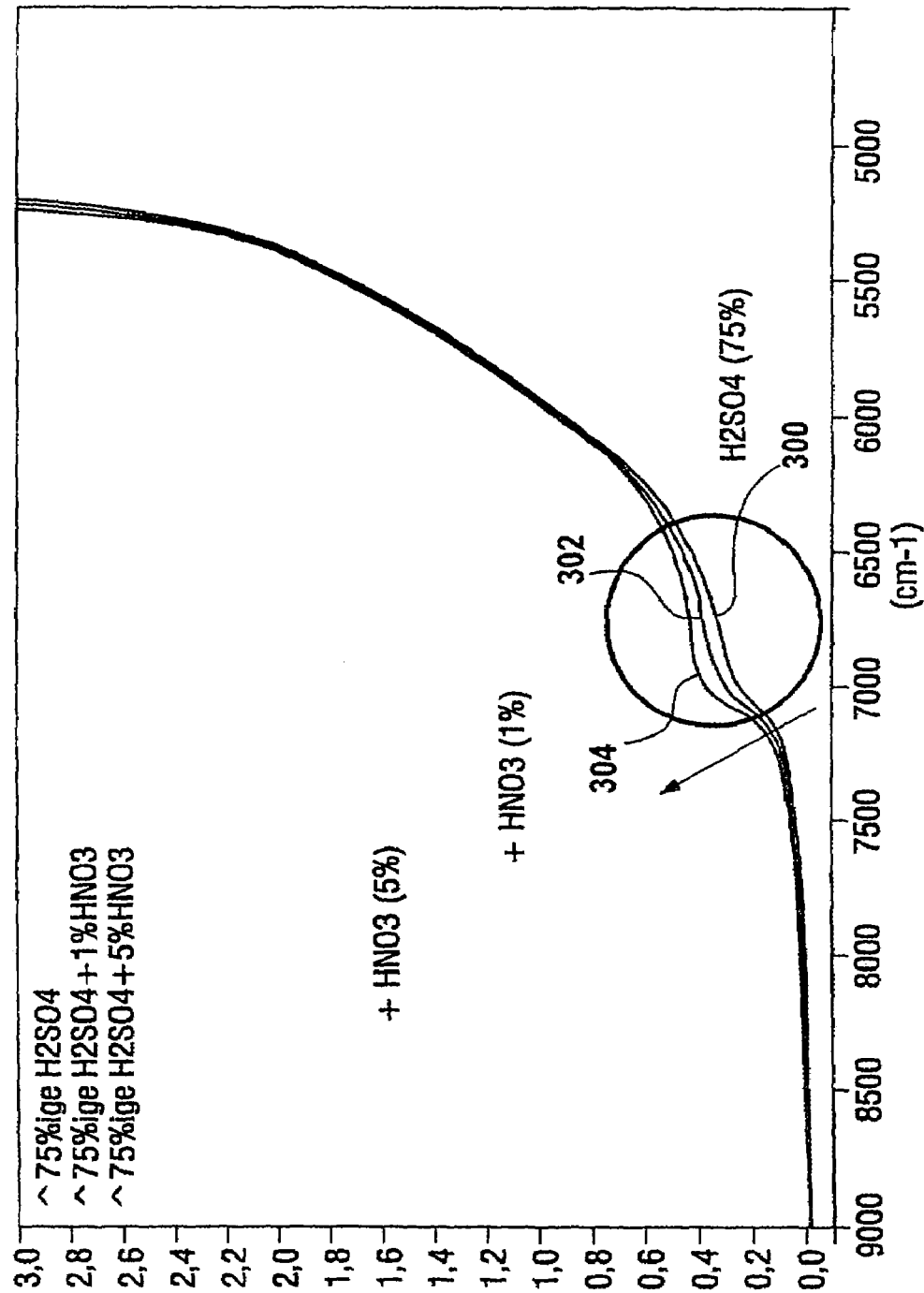
FIG. 3 shows various NIR spectra for various concentrations of nitric acid.

FIG. 3 shows the spectra 300, 302 and 304. Spectrum 300 has been recorded for 75% sulfuric acid without nitric-acid content. Spectrum 302 has been recorded for 75% sulfuric acid with 1% nitric-acid content. Spectrum 304 has been recorded for 75% sulfuric acid with 5% nitric-acid content.

The measured NIR spectra 300, 302 and 304 accordingly differ distinctly, depending on the percentage content of nitric acid in the acid phase. In corresponding manner it is possible for the nitric-acid content in the acid phase to be determined by measurement of the NIR spectrum. To this end, a matrix-specific calibration model based on comparative titration measurements is preferably used.

Figure 4:
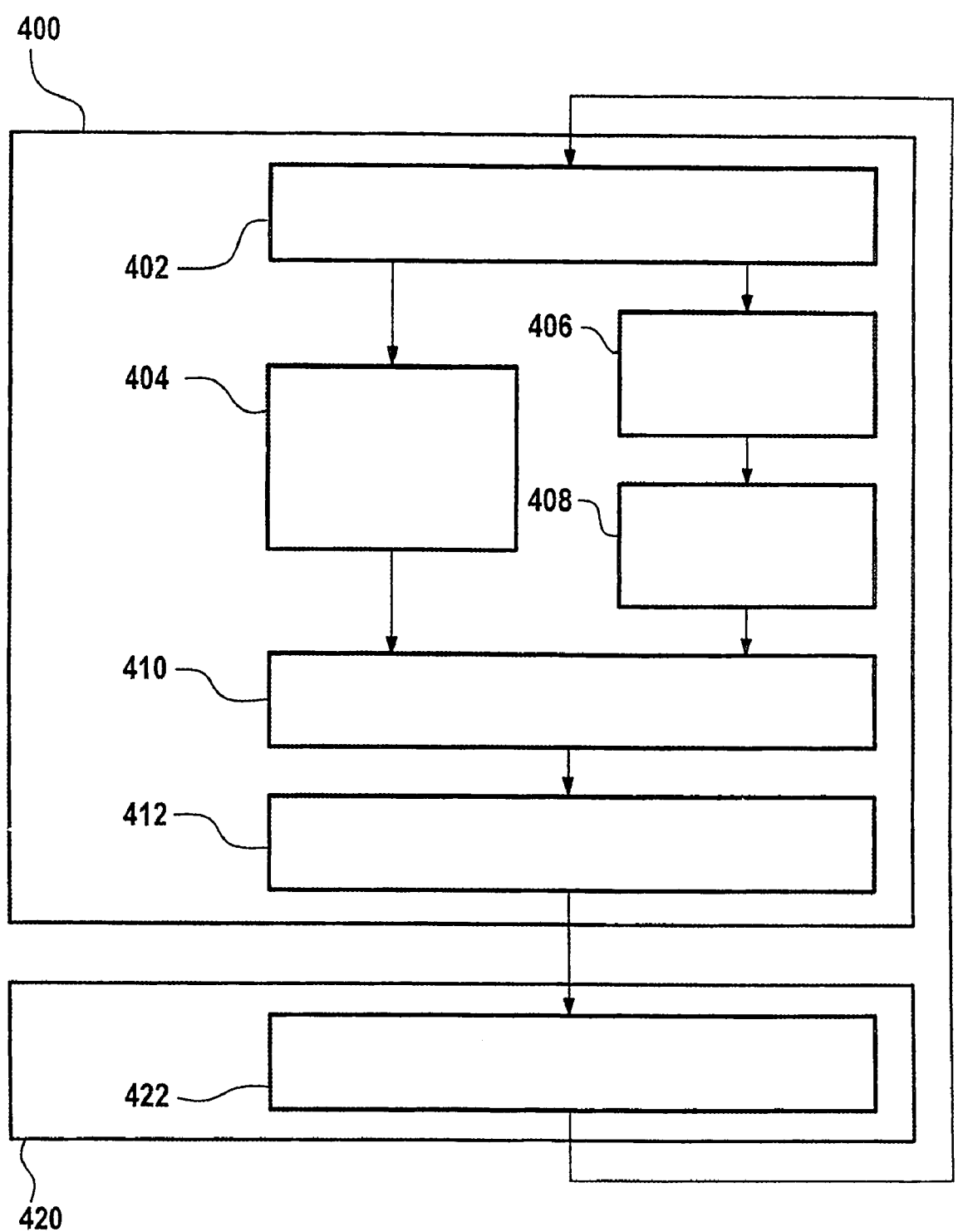
FIG. 4 is a flow chart for the process of creating the matrix-specific calibration model, the validation and enhancement thereof.

FIG. 4 illustrates the procedure for obtaining a database for the generation of a matrix-specific calibration model. Step 400 illustrates the creation of such a calibration model; step 420 illustrates the validation of this model.

Step 402 represents the physical matrix, which is process-specific and dependent on the process parameters with regard to its special composition.

The nitric-acid content, which is ascertained by means of manual sampling 406 with subsequent titration 408, is used for creation of the calibration model. Sampling and titration may also be undertaken in automated manner and online, or manually and offline. In parallel, a measuring cell, with which the NIR spectra pertaining to the samples can be recorded, is installed in the process flow. This is undertaken in step 404.

In step 410, the results from the titration determinations are compared and are correlated with the respective NIR spectra with the aid of chemometric methods.

In step 412, all of the comparisons between all of the NIR spectra and all of the titration results are combined and are correlated in a model. The parameters of the model are adapted and adjusted in such a way that the content of nitric acid for the existing substance system and the existing process parameters are reproduced optimally. Once the model has been adapted and optimized, the matrix-specific calibration model is available at the end of step 412.

Subsequently, in step 420, validation of the model is undertaken in respect of the current process. Whenever titration results are available in a manner temporally appropriate to the spectra arising from the process, said results can be integrated in accordance with step 400 for the purpose of successive enhancement of the model (step 422).

Figure 5:
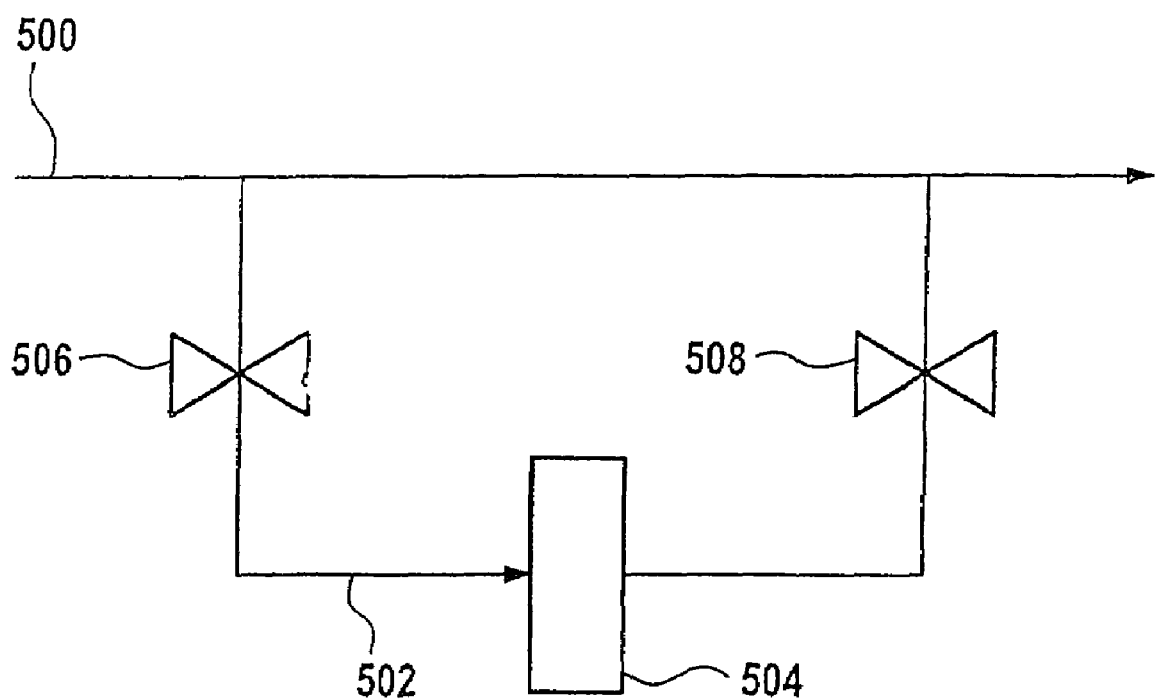
FIG. 5 is a schematic representation of a bypass with a measuring cell.

FIG. 5 shows an embodiment of the invention with a measuring-point (for example, measuring-point 215 of FIG. 2). The product stream of the current production flows through the line 500. A bypass 502 is located on the line 500. The bypass 502 has a measuring cell 504. Located upstream and downstream of the measuring cell 504 in the direction of flow is a shut-off device 506 and 508, respectively. The shut-off devices enable access to the measuring cell while the product stream is running.

LIST OF REFERENCE SYMBOLS reactor 200
toluene 201
sulfuric acid 202 nitric acid 203
measuring-point 205
optical waveguide 206
regulation of metering 207
separator 208
acid phase 209
reactor 210
mononitrotoluene (MNT) 211
sulfuric acid 212
nitric acid 213
measuring-point 215
optical waveguide 216
regulation of metering 217
separator 218
acid phase 219
NIR spectrometer 220
calibration model 222
process control system 224
organic phase 230
spectrum 300
spectrum 302
spectrum 304
line 500
bypass 502
measuring cell 504
shut-off device 506
shut-off device 508

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for monitoring and/or controlling at least one nitrating process comprising:
    a) measuring spectrometrically and online composition of an acid phase of a nitration reaction mixture,
    b) relaying data from a) to a process control system in order to monitor and to control the production process.
2. The process of claim 1 in which an infrared spectrometer is used in a).
3. The process of claim 1 in which a near infrared spectrometer is used in a).
4. The process of claim 1 in which a measuring cell for spectrometric measurement in a) is located in a by-pass.
5. The process of claim 1 in which the data are based on the spectrometric online measurement and evaluation with a matrix-specific calibration model.
6. The process of claim 5 in which a spectrum obtained by online measurement is evaluated with a matrix-specific calibration model based on comparative titration measurements.
7. The process of claims 1 to 6 in which (i) a first supply of nitric acid for mononitration is monitored and/or controlled after spectrometric examination of the mononitration reaction mixture and (ii) a second supply of nitric acid for dinitration is monitored and/or controlled after spectrometric examination of the dinitration reaction mixture.
8. The process of any of claims 1 to 6 in which an infrared spectrometer is connected to several measuring-points and is operated in multiplex mode in a) one or several nitration units.
9. The process of any of claims 1 to 6 in which a near infrared spectrometer is connected to several measuring points and is operated in multiplex mode in a) one or several nitration units.

10. A computer readable media encoded with a program capable of automatically implementing the steps of:
    a) evaluating data obtained by a spectrometric examination of an acid phase after nitration to determine the content of nitric acid in the acid phase, and
    b) relaying the nitric-acid content from a) to a regulator to control metering of nitric acid to a nitration reaction mixture.
11. The product of claim 10 having a matrix-specific calibration model for evaluating the nitric acid content data from a).
12. The product of claim 10 which is designed for automated regulation of the nitrating process.
13. A facility for monitoring and/or controlling a nitrating process comprising:
    a) means for spectrometric examination of an acid phase after a nitration, and
    b) regulating means for metering nitric acid into at least one nitrating reactor, the regulating means being designed to regulate metering of nitric acid on the basis of the spectrometric examination.
14. The facility of claim 13 in which the means for spectrometric examination comprises an infrared spectrometer.
15. The facility of claim 13 in which the means for spectrometric examination comprises a near infrared spectrometer.
16. The facility of claims 13 to 15 having a bypass downstream from at least one nitrating reactor with a measuring cell for the spectrometric examination located in the bypass.
17. The facility of any of claims 13 to 15 having means for measuring a spectrum and means for evaluating the measurement with a matrix-specific calibration model based on comparative titration measurements.
18. The facility of any of claims 13 to 15 in which the means for spectrometric measurement comprises an infrared spectrometer with electronic evaluating unit, and the infrared spectrometer is connected to several measuring-points for spectrometric examination of the acid phase after a nitration, and the infrared spectrometer is designed for multiplex operation.
19. The facility of claims 13 to 15 having a process control system for the regulating means and a connection of the means for spectrometric examination to the process control system.
20. The facility of claim 16 having means for measuring a spectrum and means for evaluating the measurement with a matrix-specific calibration model based on comparative titration measurements.
21. The facility of claim 17 in which the means for spectrometric measurement comprises an infrared spectrometer with electronic evaluating unit, and the infrared spectrometer is connected to several measuring-points for spectrometric examination of the acid chase after a nitration, and the infrared spectrometer is designed for multiplex operation.
22. The facility of claim 20 in which the means for spectrometric measurement comprises an infrared spectrometer with electronic evaluating unit, and the infrared spectrometer is connected to several measuring-points for spec trometric examination of the acid chase after a nitration, and the infrared spectrometer is designed for multiplex operation.

23. The facility of claim 18 having a process control system for the regulating means and a connection of the means for spectrometric examination to the process control system.

24. The facility of claim 20 having a process control system for the regulating means and a connection of the means for spectrometric examination to the process control system.

* * * * *